United States Patent [19]

Aya et al.

[11] Patent Number: 4,500,342
[45] Date of Patent: Feb. 19, 1985

[54] HERBICIDALLY ACTIVE SUBSTITUTED PHENYLSULFONYLUREA DERIVATIVES AND INTERMEDIATES THEREFOR

[75] Inventors: Masahiro Aya; Junichi Saito; Kazuomi Yasui, all of Tokyo; Kozo Shiokawa, Kanagawa; Norihisa Morishima, Tokyo; Toshio Goto, Kanagawa, all of Japan

[73] Assignee: Nihon Tokushu Noyaku Seizo K.K., Tokyo, Japan

[21] Appl. No.: 340,903

[22] Filed: Jan. 20, 1982

[30] Foreign Application Priority Data

Jan. 26, 1981 [JP] Japan ................................. 56-8977
Jun. 20, 1981 [JP] Japan ................................ 56-94571

[51] Int. Cl.³ ................... C07D 251/46; A01N 43/66; C07D 251/42; C07C 155/02
[52] U.S. Cl. ........................................ 71/93; 544/211; 260/545 R
[58] Field of Search .......................... 544/211; 71/93; 260/545 R

[56] References Cited

U.S. PATENT DOCUMENTS

| 4,127,405 | 11/1978 | Levitt | 71/93 |
| 4,169,719 | 10/1979 | Levitt | 71/92 |
| 4,368,069 | 1/1983 | Chen et al. | 544/211 |
| 4,378,991 | 4/1983 | Levitt | 71/93 |

FOREIGN PATENT DOCUMENTS 1514 4/1979 European Pat. Off. ............ 544/211

*Primary Examiner*—John M. Ford
*Attorney, Agent, or Firm*—Sprung, Horn, Kramer & Woods

[57] ABSTRACT

Herbicidally active substituted phenylsulfonyl urea derivatives of the formula

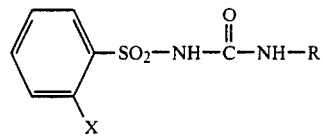

in which
X is phenyl or phenoxy,
R is

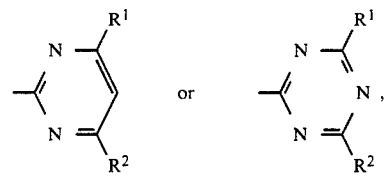

and
$R^1$ and $R^2$ each independently is methyl or methoxy.
They are made from phenylisocyanates of the formula

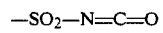

which are produced by reacting a phenylsulfonamide of the formula

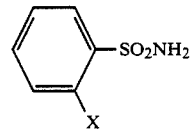

with phosgene or with trichloromethyl chloroformate in the presence of an aliphatic isocyanate.

8 Claims, No Drawings

HERBICIDALLY ACTIVE SUBSTITUTED PHENYLSULFONYLUREA DERIVATIVES AND INTERMEDIATES THEREFOR

The present invention relates to certain new substituted phenylsulfonylurea derivatives, to a process for their preparation and to their use as herbicides. The invention also relates to certain new intermediates for the preparation of the said phenylsulfonylurea derivatives and to a process for the preparation of those intermediates.

It has been disclosed in U.S. Pat. Nos. 4,127,405 and 4,169,719 and in Japanese Laid-open patent application No. 52-122384 that herbicidal activity is possessed by compounds of the general formula

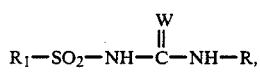

wherein
R represents

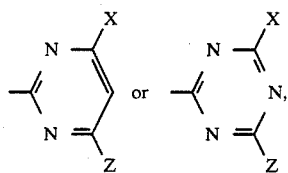

$R_1$ represents

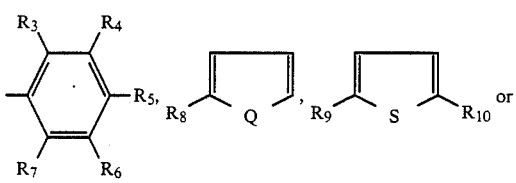

$R_3$ and $R_6$ independently represent hydrogen, fluorine, bromine, iodine, alkyl with 1-4 carbon atoms, alkoxy with 1-4 carbon atoms, nitro, trifluoromethyl, cyano, $CH_3S(O)_n$— or $CH_3CH_2S(O)_n$—, $R_4$ represents hydrogen, fluorine, chlorine, bromine or methyl, $R_5$ represents hydrogen, fluorine, chlorine, bromine, methyl or methoxy, $R_7$ represents hydrogen, fluorine, bromine, alkyl of 1-2 carbon atoms or alkoxy with 1-2 carbon atoms, $R_8$ represents hydrogen, methyl, chlorine or bromine, $R_9$ and $R_{10}$ independently represent hydrogen, methyl, chlorine or bromine, W and Q independently represent oxygen or sulfur, n is 0, 1 or 2, X represents hydrogen, chlorine, bromine, methyl, ethyl, alkoxy with 1-3 carbon atoms, trifluoromethyl, $CH_3S$— or $CH_3OCH_2$—, and Z represents methyl or methoxy, with the provisos that (a) where $R_5$ is other than hydrogen, then at least one of $R_3$, $R_4$, $R_6$ and $R_7$ must be other than hydrogen, and at least two of $R_3$, $R_4$, $R_6$ and $R_7$ must be hydrogens, (b) where $R_5$ is hydrogen and all of $R_3$, $R_4$, $R_6$ and $R_7$ are other than hydrogen, then all of $R_3$, $R_4$, $R_6$ and $R_7$ must be either chlorine or methyl, and (c) where $R_3$ and $R_7$ are both hydrogens, then at least one of $R_3$, $R_4$, $R_5$ and $R_6$ must be hydrogen, and agriculturally acceptable salts thereof.

The present invention now provides, as new compounds, the substituted phenylsulfonylurea derivatives of the general formula

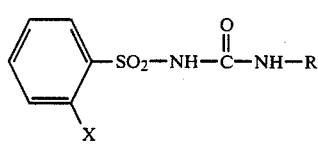

in which
X represents phenyl or phenoxy, and
R represents a group of the formula

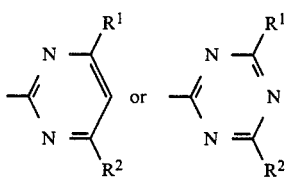

wherein
$R^1$ represents methyl or methoxy and
$R^2$ represents methyl or methoxy.

The compounds of the present invention have an excellent selective herbicidal activity.

In particular, compared with conventional herbicides that show considerable phytotoxicity towards rice plants, although showing a herbicidal effect at very low dosages, the compounds of the formula (I) show substantially no phytotoxicity towards rice plants and exhibit an accurate, selective herbicidal effect at low dosages.

The active compounds according to this invention show little or no toxicity towards warm-blooded animals and have a broad spectrum of herbicidal activity. The present invention thus represents an enrichment of the art.

The present invention also provides a process for the preparation of a compound of the formula (I), characterized in that a compound of the general formula

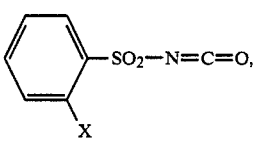

in which
X has the meaning given above, is reacted with a compound of the general formula $$H_2N—R \qquad (III),$$

in which

R has the meaning given above, if appropriate in the presence of a diluent.

Examples of the compounds of the formula (II) to be used as starting materials are 2-biphenylylsulfonyl isocyanate and
2-phenoxyphenylsulfonyl isocyanate.

Examples of the other starting materials, that is to say compounds of the formula (III), are:

2-amino-4,6-dimethylpyrimidine,
2-amino-4,6-dimethoxypyrimidine,
2-amino-4-methoxy-6-methylpyrimidine,
2-amino-4-methoxy-6-methyl-1,3,5-triazine,
2-amino-4,6-dimethoxy-1,3,5-triazine, and
2-amino-4,6-dimethyl-1,3,5-triazine.

If 2-biphenylylsulfonyl isocyanate and 2-amino-4-methoxy-6-methyl-1,3,5-triazine are used as starting materials, the course of the reaction can be represented by the following equation:

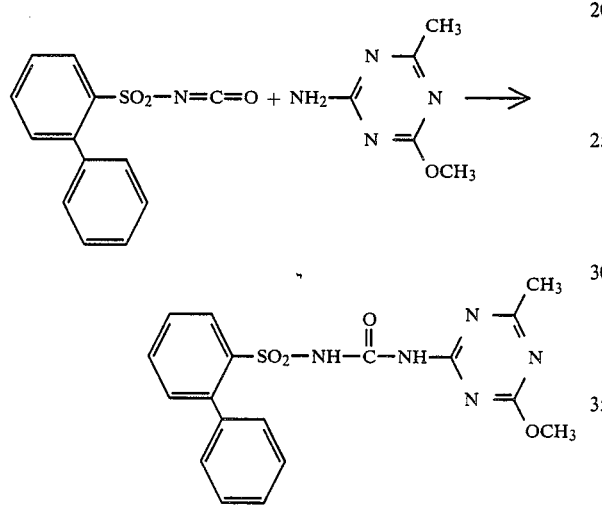

The process for preparing the compounds of this invention is preferably carried out in the presence of a diluent. For this purpose, any inert organic solvent may be employed. Examples of such solvents and diluents include aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acid amides such as dimethylformamide and dimethylacetamide; sulfones and sulfoxides, such as dimethylsulfoxide or sulfolane; and bases such as pyridine.

The process of this invention can be efficiently carried out in the presence of a catalyst, examples of which are tertiary amines, such as 1,4-diazabicyclo[2,2,2]octane.

The process of this invention can be carried out over a wide range of temperatures. Generally, it is carried out at a temperature between $-20°$ C. and the boiling point of the reaction mixture, preferably between 0° and 100° C. The reaction is preferably carried out under ambient pressure, although it can be effected under elevated or reduced pressure.

The intermediate products of the formula (II) have not hitherto been disclosed in the literature. They can be prepared by a further process according to the invention, not forming part of the state of the art, by reacting phenylsulphonamides of the general formula

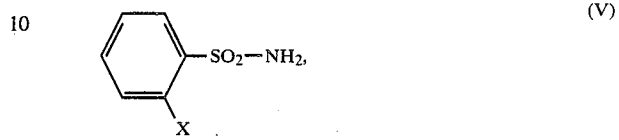

wherein

X represents phenyl or phenoxy, with phosgene ($COCl_2$) or chloroformic acid trichloromethyl ester ($CCl_3O-CO-Cl$), in the presence of an aliphatic isocyanate and, if appropriate, in the presence of a diluent.

If 2-phenoxyphenylsulphonamide and phosgene are used as the starting materials and n-butyl isocyanate as the aliphatic isocyanate, the course of the reaction can be represented by the following equation:

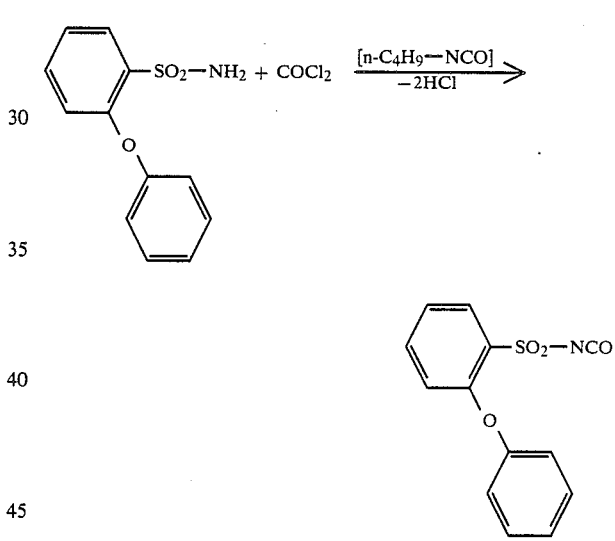

It is necessary for this reaction to be carried out in the presence of an aliphatic isocyanate; the latter can be recovered and re-employed after the completion of the reaction. It is preferable to use alkyl isocyanates having 3–8 C atoms or cycloalkyl isocyanates having 5–8 C atoms. The following may be mentioned as individual examples of these: n-butyl isocyanate, n-hexyl isocyanate and cyclohexyl isocyanate.

Suitable diluents for this process are any of the customary inert solvents, for example hydrocarbons, such as hexane, cyclohexane, petroleum ether, ligroin, toluene or xylene; chlorinated hydrocarbons, for example methylene chloride, chloroform, carbon tetrachloride, ethylene chloride, trichloroethylene or chlorobenzene; ethers, such as diethyl ether, methyl ethyl ether, diisopropyl ether, dibutyl ether, dioxane or tetrahydrofuran; ketones, for example acetone, methyl ethyl ketone, methyl isopropyl ketone or methyl isobutyl ketone; nitriles, for example acetonitrile or propionitrile; esters, for example ethyl acetate or amyl acetate; amides, for example dimethylformamide or dimethylacetamide;

sulfones and sulfoxides, such as, for example, sulfolane and dimethyl sulfoxide; and bases, for example pyridine.

It is advantageous to carry out the reaction (V)→(II) in the presence of a suitable catalyst. Suitable catalysts which should be mentioned are, in particular, tertiary amines, such as, for example, triethylamine, dimethylcyclohexylamine and 1,4-diazabicyclo[2,2,2]-octane.

The reaction temperatures in the reaction (V)→(II) can be varied within a wide range. In general, the reaction is carried out at temperatures between −20° C. and the boiling point of the reaction mixture, preferably between 80° and 150° C. In general, the reaction is carried out under normal pressure, but it can also be carried out under increased or reduced pressure.

In carrying out the reaction (V)→(II), 1-2 moles, preferably 1.05-1.3 moles, of the aliphatic isocyanate and 1-4 moles, preferably 1-1.5 moles, of phosgene or 0.5-1 mole, preferably 0.55-0.65 mole, of chloroformic acid trichloromethyl ester are generally employed per mole of phenylsulphonamide (V). The catalyst is generally employed in quantities of 0.1-5 g, preferably 0.8-2.2 g, per mole of (V).

The phenylsulphonyl isocyanates (II) may be worked up and isolated in a customary manner; these isocyanates can, for example, be purified by distillation.

The compounds of the formula (I) influence plant growth and can therefore be used as defoliants, desiccants, agents for destroying broad-leaved plants, germination inhibitors and, especially, as weed-killers. By "weeds" in the broadest sense there are meant plants growing in places where they are not desired. Whether the compounds act as total herbicides or selective herbicides depends essentially on the amount used.

The compounds according to the present invention may be used, for example, to combat the following plants: dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cyanodon, Monocharia, Fimbristylis, Sagittaria, Eleocharis, Scirpus, Paspalum, Ischaemum, Spenoclea, Dactyloctenium, Agrostis, Alopecurus and Apera.

The compounds according to the present invention may be used, for example, as selective herbicides in the following cultures: dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The present compounds are very effective when used to combat weeds occurring in paddy fields and, as stated above, show substantially no phytotoxicity to the rice plants being cultivated. The compounds can be used before, during and after the emergence of the weeds. They are especially suitable as selective herbicides when applied prior to germination, for example to the soil and/or to the stems and leaves of the weeds. As examples of paddy-field weeds there may be mentioned *Rotala indica, Lindernia procumbens, Ludwiga prostrata, Potamogeton distinctus, Elatine triandra, Echinochloa crus-galli, Monochoria vaginalis, Eleocharis acicularis, Eleocharis kuroguwai, Cyperus difformis, Cyperus serotinus, Sagittaria pygmaea, Alisma canaliculatum* and *Scirpus juncoides.*

The active compounds can be converted into the customary formulations, such as solutions, emulsions, wettable powders, suspensions, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.001 to 100 percent by weight of active compound, preferably from 0.005 to 95 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

By including other active ingredients, it is possible to obtain a broad herbicidal spectrum and an accurate control effect; a synergistic effect by mixing of these is also expected. Examples of the other active ingredients include:

2-chloro-2',6'-diethyl-N-(butoxymethyl)-acetanilide,
N-(O,O-dipropyl-diethylphosphorylacetyl)-2-methylpiperidine,
S-(4-chlorobenzyl)-N,N-diethylthiol carbamate,
S-ethyl-N,N-hexamethylenethiol carbamate,
O-methyl-O-(2-nitro-p-tolyl)-N-isopropylphosphoramide thioate,
O-ethyl-O-(2-nitro-5-methylphenyl)-N-sec-butylphosphoramide thioate,
3,4-dimethyl-2,6-dinitro-N-1-ethylpropylanilide,
α,α,α-trifluoro-2,6-dinitro-N,N-dipropyl-p-toluidine,
2-chloro-2',6'-diethyl-N-(n-propoxyethyl)acetanilide,
4,5-dichloro-1,3-thiazol-2-yloxy acetic acid N-isopropyl-N-ethoxyethoxyamide,
5-ethyl-1,3,4-thiadiazol-2-yloxy acetic acid 1',2',3',4'-tetrahydroquinolide,
benzothiazol-2-yloxy acetic acid N,N-diallylamide,
benzoxazol-2-yloxy acetic acid N-sec-butyl-N-methylamide,
benzoxazol-2-yloxy acetic acid N-cyclohexyl-N-methylamide,
benzothiazol-2-yloxy acetic acid N-methyl-N-(1-methylpropargyl)amide,
benzoxazol-2-yloxy acetic acid N-benzyl-N-propargylamide,
benzothiazol-2-yloxy acetic acid 2'-ethylpiperidide,
benzothianol-2-yloxy acetic acid 2',4'-dimethylpiperidide,
benzoxazol-2-yloxy acetic acid 2',4',6'-trimethylpiperidide,
benzoxazol-2-yloxy acetic acid hexamethylenimide,
benzothiazol-2-yloxy acetic acid perhydroindolide,
benzoxazol-2-yloxy acetic acid perhydroindolide,
benzothiazol-2-yloxy acetic acid 1',2',3',4'-tetrahydroquinolide,
benzoxazol-2-yloxy acetic acid 2'-methyl-1',2',3',4'-tetrahydroquinolide,
benzoxazol-2-yloxy acetic acid N-methylanilide,
benzothiazol-2-yloxy acetic acid N-methylanilide,
benzoxazol-2-yloxy acetic acid N-ethylanilide,
benzoxazol-2-yloxy acetic acid N-propylanilide,
benzoxazol-2-yloxy acetic acid N-isopropylanilide,
benzothiazol-2-yloxy acetic acid N-methyl-N-2'-methoxyanilide,
benzoxazol-2-yloxy acetic acid N-methyl-N-2'-methoxyanilide,
benzoxazol-2-yloxy acetic acid N-methyl-N-2'-trifluoromethylanilide,
benzothiazol-2-yloxy acetic acid N-methyl-N-2'-chloroanilide,
benzoxazol-2-yloxy acetic acid N-methyl-N-2'-chloroanilide,
benzothiazol-2-yloxy acetic acid N-methyl-N-2'-fluoroanilide,
benzoxazol-2-yloxy acetic acid N-methyl-N-2'-fluoroanilide,
benzothiazol-2-yloxy acetic acid N-methyl-N-3'-methylanilide,
benzoxazol-2-yloxy acetic acid N-methyl-N-3'-methylanilide,
benzothiazol-2-yloxy acetic acid N-methyl N-3'methoxyanilide,
benzoxazol-2-yloxy acetic acid N-methyl-N-3'-methoxyanilide,
benzothiazol-2-yloxy acetic acid N-methyl-N-3'-isopropoxyanilide,
benzoxazol-2-yloxy acetic acid N-methyl-N-3'-isopropoxyanilide,
benzothiazol-2-yloxy acetic acid N-methyl-3'-trifluoromethylanilide,
benzoxazol-2-yloxy acetic acid N-methyl-N-3'-trifluoromethylanilide,
benzothiazol-2-yloxy acetic acid N-methyl-N-3'-chloroanilide,
benzoxazol-2-yloxy acetic acid N-methyl-N-3'-chloroanilide,
benzothiazol-2-yloxy acetic acid N-methyl-N-3'-fluoroanilide,
benzoxazol-2-yloxy acetic acid N-methyl-N-3'-fluoroanilide,
benzothiazol-2-yloxy acetic acid N-methyl-N-3'-bromoanilide,
benzoxazol-2-yloxy acetic acid N-methyl-N-3'-bromoanilide,
benzoxazol-2-yloxy acetic acid N-methyl-N-4'-methylanilide,
benzoxazol-2-yloxy acetic acid N-methyl-N-4'-methoxyanilide,
benzoxazol-2-yloxy acetic acid N-methyl-N-4'-fluoroanilide,
benzoxazol-2-yloxy acetic acid N-methyl-N-2',3'-dimethylanilide,
benzoxazol-2-yloxy acetic acid N-methyl-N-2',3'-dichloroanilide,
benzoxazol-2-yloxy acetic acid N-methyl-N-4'-chloro-2'-methylanilide,
benzothiazol-2-yloxy acetic acid N-methyl-N-2',5'-dichloroanilide,
benzoxazol-2-yloxy acetic acid N-methyl-N-2',5'-dichloroanilide,
benzothiazol-2-yloxy acetic acid N-methyl-N-3',5'-dimethylanilide,
benzoxazol-2-yloxy acetic acid N-methyl-N-3',5'-dimethylanilide,
benzothiazol-2-yloxy acetic acid N-methyl-N-3',5'-ditrifluoromethylanilide,
benzoxazol-2-yloxy acetic acid N-methyl-N-5'-indanylamide,
benzothiazol-2-yloxy acetic acid N-methyl-N-3'-ethylanilide, benzoxazol-2-yloxy acetic acid N-methyl-N-3'-ethylanilide, and benzothiazol-2-yloxy acetic acid N-isopropylanilide.

The active compounds can be used as such, in the form of their formulations or in the use forms prepared therefrom by further dilution, such as ready-to-use solutions, suspensions, emulsions, powders, pastes and granules. They may be used in the customary manner, for example by watering, spraying, atomizing, scattering or dusting.

The amount of active compound in the ready-to-use preparations can vary widely according to circumstance. However, it is in general from 0.01 to 95 percent, preferably from 0.05 to 60 percent by weight.

The compounds can also be used in the ultra-low-volume method, wherein the preparation used can contain up to 100% of the active ingredient.

The active compounds can be applied after emergence of the plants or before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 3 kg of active compound per hectare, preferably between 0.2 and 1 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The following examples serve to illustrate the invention further.

The preparation of the intermediates (II) is illustrated by the following examples:

EXAMPLE 1

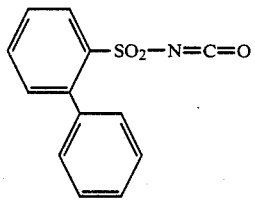

23.3 g of 2-biphenylylsulfonamide, 10.9 g of n-butyl isocyanate, a catalytic amount of 1,4-diazabicyclo[2,2,2]-octane and 150 ml of xylene were refluxed with stirring for an hour. Then, a solution of 11.9 g of trichloromethyl chloroformate in 30 ml of xylene was added dropwise over 2.5 hours while maintaining the internal temperature at 120°–125° C. After this addition, the mixture was held at this temperature for a while, and thereafter the mixture was refluxed for a short period to complete the reaction. At the end of the reaction, the xylene and n-butyl isocyanate were distilled off under reduced pressure, to obtain 22.0 g of 2-biphenylylsulfonylisocyanate of high purity. B.pt. 135°–137° C./0.7–0.8 mmHg.

EXAMPLE 2

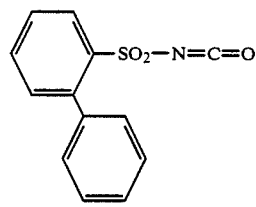

23.3 g of 2-biphenylylsulfonamide, 10.9. g of n-butyl isocyanate, a catalytic amount of 1,4-diazabicyclo[2,2,2]-octane and 180 ml of chlorobenzene were refluxed with stirring for 2 hours. Then, phosgene in a slight excess of the theroretical amount was blown through the reaction mixture over 2 hours while maintaining the internal temperature at 115°–120° C. At this time, any unreacted phosgene escaping from the reaction system was trapped in a dry ice trap and returned to the reactor. After addition of the phosgene, the reaction mixture was further stirred at the reflux temperature for a short time to complete the reaction. The mixture was cooled, and if necessary, it was filtered under reduced pressure to remove the insoluble matter. It was then concentrated under reduced pressure, to obtain 20.0 g of 2-biphenylylsulfonylisocyanate. B.p. 135°–137° C./0.7–0.8 mmHg.

EXAMPLE 3

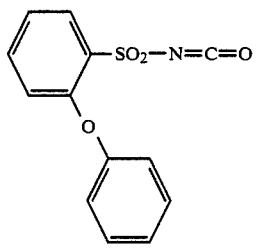

25.0 g of 2-phenoxyphenylsulfonamide, 14.0 g of n-hexyl isocyanate, a catalytic amount of 1,4-diazabicyclo[2,2,2]-octane and 150 ml xylene were refluxed with stirring for an hour. Thereafter, the mixture was reacted with a solution of 11.9 g of trichloromethyl chloroformate in 30 ml of xylene in a manner similar to that of Example (1). At the end of the reaction, the xylene and n-hexyl isocyanate were distilled off, to obtain 22.8 g of 2-phenoxyphenylsulfonylisocyanate. B.p. 146°–150° C./0.7 mmHg.

EXAMPLE 4

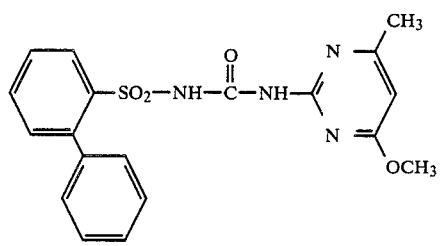

13.9 g of 2-amino-4-methoxy-6-methylpyrimidine were dissolved in 150 ml of dry dichloromethane. To this solution was added dropwise a solution of 28.5 g of 2-biphenylylsulfonyl isocyanate in 40 ml of toluene over an hour. During this addition, the internal temperature was maintained at room temperature. When the addition was finished, the mixture was stirred at room temperature for 10 hours to complete the reaction. After completion of the reaction, the mixture was concentrated to about half the volume by evaporating dichloromethane under reduced pressure. The resultant colorless crystals were filtered. The crystals were then washed with a small amount of ether and dried to obtain 34.6 g of N-2-biphenylylsulfonyl-N'-(4-methoxy-6-methylpyrimidin-2-yl)urea; m.p. 199°–202° C.

EXAMPLE 5

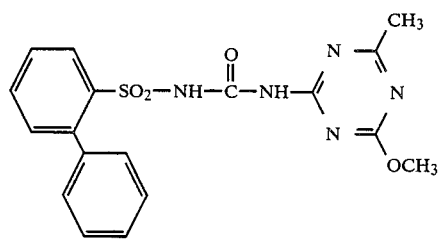

14.0 g of 2-amino-4-methoxy-6-methyl-1,3,5-triazine were suspended in 100 ml of dry acetonitrile, and then 0.1 g of 1,4-diazabicyclo[2,2,2]octane was added thereto. To this mixture was added dropwise a solution of 28.5 g of 2-biphenylylsulfonyl isocyanate in 30 ml of xylene over an hour. During this addition, the reaction was accompanied by slight heat generation, and therefore cooling was applied as necessary. After the addition, the reaction was continued at room temperature for 5 hours and then at 40° C. for 5 hours. After allowing the mixture to cool to room temperature, the precipitated colorless crystals were filtered, washed with ether and dried to obtain 33.9 g of N-2-biphenylylsulfonyl-N'-(4-methoxy-6-methyl-1,3,5-triazin-2-yl)urea; m.pt. 190°–193° C.

The compounds of this invention shown in Table 1 were produced in a manner similar to that described above:

TABLE 1

$$\text{Ar}-SO_2-NH-\overset{\overset{O}{\|}}{C}-NH-R \quad (I)$$

with X substituent on the phenyl ring.

| Compound No. | X | R | Melting point (°C.) |
|---|---|---|---|
| 3 | phenyl | 4,6-dimethylpyrimidin-2-yl | 203–208 |
| 4 | phenoxy | 4,6-dimethylpyrimidin-2-yl | 178–180 |
| 5 | phenoxy | 4-methoxy-6-methylpyrimidin-2-yl | 196–200 |
| 6 | phenoxy | 4-methoxy-6-methyl-1,3,5-triazin-2-yl | 185–190 |
| 7 | phenyl | 4,6-dimethoxypyrimidin-2-yl | 175–180 |
| 8 | phenoxy | 4,6-dimethoxy-1,3,5-triazin-2-yl | 160–165 |

Compositions according to this invention are illustrated in the following examples.

In these examples the compounds according to the present invention are each identified by the number (given in brackets) from Examples 4 and 5 and Table 1.

EXAMPLE 6

Fifteen parts of compound (1), 80 parts of a 1:5 mixture of powdered diatomaceous earth and powdered clay, 2 parts of sodium alkylbenzenesulfonate and 3 parts of sodium alkylnaphthalenesulfonate/formaldehyde condensate were ground and mixed to form a wettable powder. The wettable powder was diluted with water before use.

EXAMPLE 7

Thirty parts of compound (2), 55 parts of xylene, 8 parts of polyoxyethylene alkylphenyl ether and 7 parts of calcium alkylbenzenesulfonate were mixed with stirring to form an emulsifiable concentrate. The emulsifiable concentrate was diluted with water before use.

EXAMPLE 8

Two parts of compound (3) and 98 parts of powdered clay were pulverized and mixed to form a dusting agent.

EXAMPLE 9

1.5 parts of compound (4), 0.5 part of isopropyl hydrogen phosphate (PAP) and 98 parts of powdered clay were ground and mixed to form a dusting agent.

EXAMPLE 10

25 parts of water were added to, and thoroughly mixed with, a mixture of 10 parts of compound (5), 30 parts of bentonite (montmorillonite), 58 parts of talc and 2 parts of lignin sulfonate. The resultant mixture was formed into granules having a size of 10 to 40 mesh by means of an extrusion-type granulator, and dried at 40° to 50° C. to form granules.

EXAMPLE 11

A rotary mixer was charged with 95 parts of clay mineral particles having a particle size distribution in the range of 0.2 to 2 mm, and, while rotating the mixer, 5 parts of compound (6) dissolved in an organic solvent were sprayed uniformly onto the clay mineral particles. The particles were then dried at 40° to 50° C. to form granules.

The herbicidal activity of the compounds of the formula (I) is illustrated by the following examples wherein the known comparison compound is identified as follows:

$$(Z) = \text{2-Cl-C}_6\text{H}_4\text{-SO}_2\text{-NH-CO-NH-(4-methoxy-6-methyl-1,3,5-triazin-2-yl)}$$

N-2-Chlorophenylsulfonyl-N'-(4-methoxy-6-methyl-1,3,5-triazin-2-yl)urea (a compound described in Japanese Laid-open Patent Application No. 52-122384)

EXAMPLE 12

Test against aquatic paddy-field weeds by treating the soil and stems and leaves under irrigation conditions (pot test)

Preparation of an active compound

Carrier: 5 parts by weight of acetone
Emulsifier: 1 part by weight of benzyloxy polyglycol ether A preparation of the active compound was obtained as an emulsifiable concentrate by mixing 1 part by weight of the active compound with the aforesaid amounts of the carrier and emulsifier. A predetermined amount of the preparation was obtained by dilution with water.

Test procedure

Wagner pots (1/5,000 are) were filled with paddy-field soil, and two rice seedlings (variety: Kinmaze) at the 2–3 leaf stage (plants about 10 cm in height) were transplanted in each pot. Seeds of *Echinochloa crus-galli, Cyperus iria, Monochoria vaginalis, Scirpus juncoides* and certain broad-leaved weeds, small pieces of *Eleocharis acicularis* and tubers of *Cyperus serotinus* and *Sagittaria pygmaea* were put into the pots, and the pots were maintained in a wet condition. When the *Echinochloa crus-galli* had grown to approximately the two-leaf stage (about 7 to 9 days after the sowing), the pots were filled with water to a depth of about 6 cm, and a predetermined amount of the active compound in the form of an emulsion was applied to the water by means of a pipette. After the treatment, the water was allowed to leak from the pots at a rate of 2 to 3 cm per day for two days. Then, the depth of water in the pots was maintained at about 3 cm, and four weeks after the treatment with the active compound, the herbicidal effect and the degree of phytotoxicity were evaluated on a scale of from 0 to 5 in accordance with the following standards.

The herbicidal effect was evaluated as follows in comparison with an untreated control.

| Rating | Weed-kill ratio based on the control |
|---|---|
| 5: | at least 95% (withered) |
| 4: | at least 80% but less than 95% |
| 3: | at least 50% but less than 80% |
| 2: | at least 30% but less thean 50% |
| 1: | at least 10% but less than 30% |
| 0: | less than 10% (not effective) |

The phytotoxicity towards the rice plants was evaluated as follows in comparison with the untreated control.

| Rating | Phytotoxicity rate in comparison with the control |
|---|---|
| 5: | at least 90% (fatal damage) |
| 4: | at least 50% but less than 90% |
| 3: | at least 30% but less than 50% |
| 2: | at least 10% but less than 30% |
| 1: | more than 0 but less than 10% |
| 0: | 0% (no phytotoxity) |

The test results are shown in Table 2, in which the symbols A to H represent the following weeds:
A: *Echinochloa crus-galli Beauv.* var
B: *Eleocharis acicularis L.*
C: *Cyperus iria L.*
D: *Scirpus juncoides Roxburgh* var.
E: *Monochoria vaginalis Presl.*
F: broad-leaved weeds (including *Lindernia procumbens Philcox, Rotala indica Koehne, Elatine triandra Schk*).
G: *Cyperus serotinus Rottboel*
H: *Sagittaria pygmaea Miq.*

TABLE 2

| Compound | Amount of the active ingredient kg/ha | Herbicidal effect | | | | | | | | Phytotoxicity Rice |
|---|---|---|---|---|---|---|---|---|---|---|
| | | A | B | C | D | E | F | G | H | |
| (1) | 0.2 | 5 | 5 | 5 | 5 | 5 | 5 | 5 | 5 | 0 |
| (2) | 0.2 | 5 | 5 | 5 | 5 | 5 | 5 | 5 | 5 | 0 |
| (3) | 0.2 | 5 | 5 | 5 | 5 | 5 | 5 | 5 | 5 | 0 |
| (4) | 0.2 | 5 | 5 | 5 | 5 | 5 | 5 | 5 | 5 | 0 |
| (5) | 0.2 | 5 | 5 | 5 | 5 | 5 | 5 | 5 | 5 | 0 |

TABLE 2-continued

| Compound | Amount of the active ingredient kg/ha | Herbicidal effect A | B | C | D | E | F | G | H | Phytotoxicity Rice |
|---|---|---|---|---|---|---|---|---|---|---|
| (6) | 0.2 | 5 | 5 | 5 | 5 | 5 | 5 | 5 | 5 | 0 |
| (7) | 0.2 | 5 | 5 | 5 | 5 | 5 | 5 | 5 | 5 | 0 |
| (8) | 0.2 | 5 | 5 | 5 | 5 | 5 | 5 | 5 | 5 | 0 |
| (Z) | 0.2 | 5 | 5 | 5 | 5 | 5 | 5 | 3 | 5 | 4 |

It will be understood that the specification and examples are illustrative but not limitative of the present invention and that other embodiments within the spirit and scope of the invention will suggest themselves to those skilled in the art.

We claim:

1. A phenoxyphenylsulfonylurea derivative of the formula

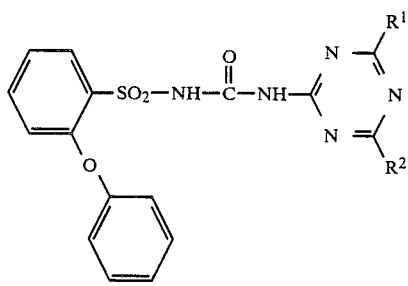

in which $R^1$ and $R^2$ each independently is methyl or methoxy.

2. A compound according to claim 1, wherein such compound is N-2-phenoxyphenylsulfonyl-N'-(4-methoxy-6-methyl-1,3,5-triazin-2-yl)urea of the formula

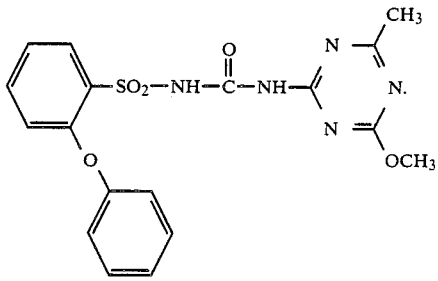

3. A compound according to claim 1, wherein such compound is N-2-phenoxyphenylsulfonyl-N'-(4,6-dimethoxy-1,3,5-triazin-2-yl)urea of the formula

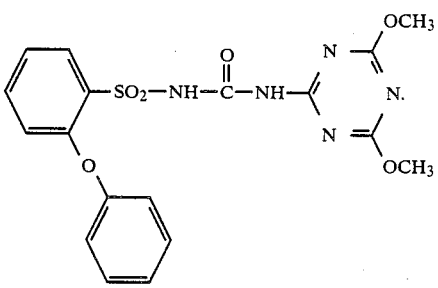

4. A herbicidal composition comprising a herbicidally effective amount of a compound according to claim 1, in admixture with a diluent.

5. A method of combating weeds, comprising applying to the weeds, or to a habitat thereof, a herbicidally effective amount of a compound according to claim 1.

6. The method according to claim 5, wherein such compound is
N-2-phenoxyphenylsulfonyl-N'-(4-methoxy-6-methyl-1,3,5-triazin-2-yl)urea, or
N-2-phenoxyphenylsulfonyl-N'-(4,6-dimethoxy-1,3,5-triazin-2-yl)urea.

7. In the cultivation of rice in a paddy field, the method for selectively controlling the growth of undesired plants in said field which comprises applying to the field a herbicidally effective amount of a compound according to claim 1.

8. 2-Phenoxyphenylsulfonyl isocyanate of the formula

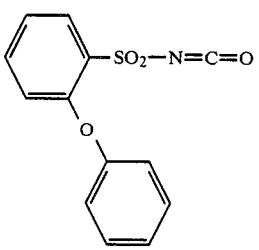

* * * * *

UNITED STATES PATENT AND TRADEMARK OFFICE
CERTIFICATE OF CORRECTION

PATENT NO. : 4,500,342
DATED : February 19, 1985
INVENTOR(S) : Masahiro Aya, et al.

It is certified that error appears in the above—identified patent and that said Letters Patent is hereby corrected as shown below:

Title Page, Abstract, line 11 — Delete formula and substitute:

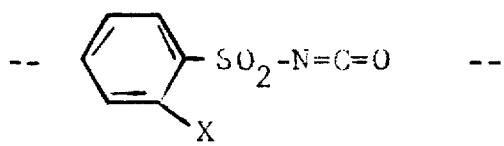

Signed and Sealed this

Second Day of December, 1986

*Attest:*

DONALD J. QUIGG

*Attesting Officer*  *Commissioner of Patents and Trademarks*